United States Patent [19]

Miyano et al.

[11] 4,064,133
[45] Dec. 20, 1977

[54] CYCLOHEXENONE DERIVATIVES

[75] Inventors: Seiji Miyano; Nobuhiro Abe, both of Fukuoka, Japan

[73] Assignee: Takeda Chemical Industries, Ltd., Osaka, Japan

[21] Appl. No.: 530,843

[22] Filed: Dec. 9, 1974

Related U.S. Application Data

[62] Division of Ser. No. 354,139, April 24, 1973, Pat. No. 3,969,409.

[30] Foreign Application Priority Data

May 11, 1972  Japan .................................. 47-47047
Dec. 22, 1972  Japan .................................. 48-2613

[51] Int. Cl.² ......................................... C07D 211/32
[52] U.S. Cl. ........................... 260/293.79; 260/293.78; 260/293.65
[58] Field of Search ...................... 260/293.79, 293.65, 260/293.78

[56] References Cited
U.S. PATENT DOCUMENTS 3,100,205  8/1963  Schulte et al. ................... 260/293.65
3,217,010  11/1965  Kuhnis et al. ................... 260/293.65

Primary Examiner—Norma S. Milestone
Attorney, Agent, or Firm—Wenderoth, Lind & Ponack

[57] ABSTRACT

Novel cyclohexenone derivatives, which are shown by the general formula

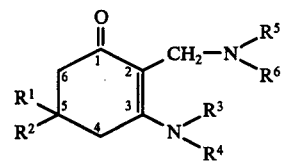

wherein each of $R^1$ and $R^2$ represents a hydrogen atom, lower alkyl or phenyl group; one of $R^3$ and $R^4$ represents a hydrogen atom or lower alkyl group, and the other represents an unsubstituted or substituted phenyl, lower alkyl or aralkyl group, or $R^3$ and $R^4$, taken together with the adjacent nitrogen atom, form a 5 to 6-membered heterocyclic ring; one of $R^5$ and $R^6$ represents a hydrogen atom or lower alkyl group, and the other represents a lower alkyl, phenyl or aralkyl group, or $R^5$ and $R^6$, taken together with the adjacent nitrogen atom, form an unsubstituted or substituted 5 to 6-membered heterocyclic ring, and their pharmaceutically acceptable salts, useful medicines such as analgesics.

12 Claims, No Drawings

CYCLOHEXENONE DERIVATIVES

This is a division of application Ser. No. 354,139, filed Apr. 24, 1973, (now U.S. Pat. No. 3,969,409, issued July 13, 1976).

The present invention relates to novel cyclohexenone derivatives having useful pharmacological actions such as analgesic action, which are shown by the general formula (I)

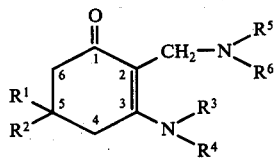

wherein each of $R^1$ and $R^2$ represents a hydrogen atom, lower alkyl or phenyl group; one of $R^3$ and $R^4$ represents a hydrogen atom or lower alkyl group, and the other represents an unsubstituted or substituted phenyl, lower alkyl or aralkyl group, or $R^3$ and $R^4$, taken together with the adjacent nitrogen atom, form a 5 to 6-membered heterocyclic ring; one of $R^5$ and $R^6$ represents a hydrogen atom or lower alkyl group, and the other represents a lower alkyl, phenyl or aralkyl group, or $R^5$ and $R^6$, taken together with the adjacent nitrogen atom, form an unsubstituted or substituted 5 to 6-membered heterocyclic ring, and their pharmaceutically acceptable salts.

The present invention relates also to a process for the production of these cyclohexenone derivatives.

Hitherto, there have been many kinds of analgesics, and some of them have been put into practical use. However, aforesaid analgesics are not satisfactory in view of some drawbacks such as showing rather weak analgesic action.

Under these circumstances, the present inventors have made extensive studies and succeeded in synthesizing novel cyclohexenone derivatives (I) defined above. And the present inventors have also unexpectedly found that these compounds have an analgesic action as well as, for example, sedative, tranquilizing, antipyretic, anticonvulsive and antitussive actions in mammals, and moreover that these compounds have an action to depress blood sugar level in mammals.

The present invention has been accomplished on the basis of these findings.

Thus, the principal object of the present invention is to provide the cyclohexenone derivatives (I) and their pharmaceutically acceptable salts useful as analgesics, sedatives, tranquilizer, antipyretics, anticonvulsant, antitussives and drugs for treatment of diabetes, and another object of the present invention is to provide a method for the production of these compounds.

In the general formula (I), the lower alkyl group represented by the symbols $R^1$ to $R^6$ respectively may be any of saturated, unsaturated, straight, branched or cyclic ones having 1 to 6 carbon atoms. Typical examples of the saturated, unsaturated) straight or branched alkyl group may be methyl, ethyl, propyl, isopropyl, allyl, 1-propenyl, butyl, isobutyl, sec-butyl, tertbutyl, pentyl or hexyl group, and typical examples of the cycloalkyl group may be cyclopropyl, cyclobutyl, cyclopentyl or cyclohexyl group. Among these alkyl groups, a lower alkyl group of about 1 to 4 carbon atoms is preferable from the practical point of view.

The aralkyl group represented by the symbols $R^3$ to $R^6$ respectively may, for example, be benzyl or phenethyl group. The 5 to 6-membered heterocyclic ring which is formed by $R^3$ and $R^4$ or by $R^5$ and $R^6$, as they are taken together with the corresponding adjacent nitrogen atom, may be that containing 1 to 2 hetero atoms (e.g. oxygen atom and nitrogen atom), such as pyrrolidino, morpholino, piperazino, piperidino and so forth.

When the phenyl group represented by the symbol $R^3$ or $R^4$ and/or the 5 to 6-membered heterocyclic ring formed by $R^5$ and $R^6$ are substituted, the substituents of these phenyl and/or heterocyclic ring are exemplified by lower alkyl groups having 1 to 3 carbon atoms, which may have hydroxyl group(s), (e.g. methyl, hydroxymethyl, ethyl, 2-hydroxyethyl, propyl, isopropyl, 3-hydroxypropyl, etc.), lower alkoxy groups having 1 to 3 carbon atoms (e.g. methoxy, ethoxy, propoxy, isopropoxy, etc.), halogen atoms (chlorine, bromine, iodine and fluorine), nitro, hydroxyl, mono- or di- lower alkyl substituted amino groups whose alkyl moiety moiety is that having 1 to 2 carbon atoms (e.g. dimethylamino, diethylamino, methylamino, ethylamino, etc.), lower acylamino groups whose alkyl moiety is that having 1 to 2 carbon atoms (e.g. acetylamino, propionylamino, etc.) and so forth. These substituents may occur in any optional number, preferably 1 or 2 and in any optional positions on the phenyl and/or heterocyclic ring.

In the present invention, the object compounds (I) are produced by the process described below:

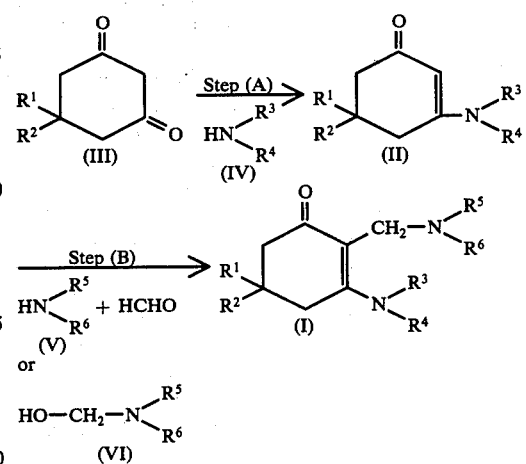

wherein $R^1$ to $R^6$ are as defined above.

The process of Step (A) is carried out by reacting a dione compound (III) with an amine compound (IV). The amount of the compound (IV) is one or more moles per mole of the compound (III), and there is practically no upper limit thereof. However, it is usually desirable to employ about 1 to about 3 moles and, more preferably, about 1 to about 1.5 mole of the compound (IV) per mole of the compound (III). The reaction of this step (Step (A)) is ordinarily conducted in a solvent, and as the solvent, any one may be employed if it is not determental to the reaction. As these solvents, there may, for example, be water, aliphatic hydrocarbons or halogenated aliphatic hydrocarbons (e.g. pentane, hexane, cyclohexane, dichloromethane, dichloroethane, chloroform, carbon tetrachloride, etc.), aromatic hydrocarbons (e.g. benzene, toluene, xylene, nitrobenzene, etc.), ethers (e.g. ethyl ether, tetrahydrofuran, isopropyl ether, dioxane, etc.), alcohols (e.g. methanol, ethanol, propanol, isopropanol, butanol, etc.), dimethylformamide and the like. The reaction may also be conducted in the absence of a solvent by using an excess amount of the compound (IV), because the excess of the compound (IV) acts as the reaction solvent in this step. While the reaction conditions such as temperature and time are not critical, it is generally advisable to conduct the reaction at a temperature near the boiling point of the reaction solvent used or of the amine compound (IV) for about 0.5 to about 2 hours. But, if necessary one may conduct the reaction at temperatures higher than or below the boiling point of the solvent used or the amine compound (IV) for an extended period of time. Moreover, while the reaction of this step can be conducted by merely allowing the compound (III) to contact with the compound (IV), the reaction may be accelerated and conducted more smoothly by employing a suitable condensing agent such as anhydrous potassium carbonate, anhydrous sodium carbonate, p-toluenesulfonic acid, calcium chloride or acetic acid or, alternatively, or employing an aromatic hydrocarbon (e.g. benzene, toluene or xylene) as the solvent and subjecting the by-produced water to azeotropic distillation. The resulting compound (II) can be isolated and purified by per se conventional means (e.g. extraction, distillation, recrystallization, chromatography, etc.).

The process of Step (B) is carried out by reacting the aminocyclohexenone compound (II) obtained in Step (A) (i) with the amine compound (V) and formaldehyde [hereinafter this reaction is referred to reaction of Step (B)-(i)], or (ii) with the aminomethanol compound (VI) [hereinafter this reaction is referred to reaction of Step (B)-(ii)].

In the reaction of Step (B)-(i), the amount of the compound (V) or formaldehyde is generally one or more moles per mole of the compound (II), and there is practically no upper limit thereof. However, for practical purposes, it is desirable to employ about 1 to about 2 moles of the compound (V) or formaldehyde per mole of the compound (II). The formaldehyde employable in this reaction may be paraformaldehyde. Moreover, while in the reaction the compound (V) is ordinarily employed in a form of hydrochloride, the compound may also be employed in a form of free base with or without hydrochloric acid of a suitable concentration (e.g. about 20 to about 40% by weight). The reaction of Step (B)-(i) is preferably conducted in a solvent and at room temperature for about 0.5 to about 100 hours. As the solvent, any one may be employed if it is not detrimental to the reaction, and there may be exemplified by the same solvents as employed in the reaction of Step (A). The reaction conditions such as temperature and time are not critical, and the reaction may be, if necessary, conducted at a temperature either higher than or below a room temperature for an extended period of time. Moreover while the reaction of Step (B)-(i) can be conducted by merely allowing to contact with the compound (II), compound (V) and formaldehyde each other, the reaction may be accelerated and conducted more smoothly by employing the condensing agents similar to those mentioned for the reaction of Step (A).

In the reaction of Step (B)-(ii), the amount of the compound (VI) is generally one or more moles per mole of the compound (II), and there is practically no upper limit thereof. However, for practical purposes, it is desirable to employ about 1 to about 2 moles of the compound (VI) per mole of the compound (II). The reaction of Step (B)-(ii) is preferably conducted in a solvent and at room temperature for about 0.5 to about 50 hours. As the solvent, any one may be employable if it is not detrimental to the reaction, and there may be exemplified by the same solvents as employed in the reaction of Step (A). The reaction conditions such as temperature and time are not critical, and the reaction may be, if necessary, conducted at a temperature either higher than or below a room temperature for an extended period of time. On some occasion, the reaction may be accelerated and conducted more smoothly by employing a condensing agent similar to those mentioned for the reaction of Step (A).

The thus produced object compounds (I) can be isolated and purified by per se conventional procedures (e.g. extraction, distillation, recrystallization, chromatography, etc.). When the compounds (II) or the object compounds (I) are free bases, they may be converted to the corresponding acid addition salts by per se conventional procedures, which may involve the use of a suitable acid, e.g. an inorganic acid (hydrochloric acid, sulfuric acid, nitric acid, phosphoric acid, carbonic acid, hydrobromic acid, etc.) or an organic acid (acetic acid, oxalic acid, succinic acid, maleic acid, fumaric acid, malic acid, tartaric acid, malonic acid, citric acid, etc.) (for example, by contacting the base with such an acid in a solvent similiar to that used in the above reactions of Steps (A) and (B)). On the contrary, if necessary, the acid addition salts of the compounds (I) may be converted to the corresponding free bases by per se conventional means such as hydrolyzing the salts with a suitable basic substance (e.g. sodium hydroxide, sodium carbonate).

The object compounds (I) or their salts which can thus be obtained by the process of this invention have pharmacological actions such as analgesic, sedative, tranquillizing, antipyretic, anticonvulsive and antitussive actions in mammals and moreover have an action to depress the blood sugar levels in mammals, and therefore, are of use as such drugs as analgesics, sedatives, tranquillizers, antipyretics, anticonvulsants, antitussives and drugs for the treatment of diabetes. Further, compound of the general formula (II) are not only useful as intermediates for the synthesis of various drugs including compounds (I), but the compounds (II) or salts thereof have pharmacological actions such as analgesic and sedative actions as do the compounds (I), and, therefore, are of use as drugs such as analgesics, sedatives and the like.

When the compounds (I) or the salts thereof are used as drugs of the type mentioned above, they may be administered per se or in the form of a pharmaceutically acceptable composition in admixture with a suitable and conventional inert vehicle or adjuvant either orally or parenterally. The pharmaceutical composition may take the form of powders, granules, tablets, capsules, solutions, suppositories, injections and so forth.

While the usual daily dosages of the compound (I) or the salt thereof depends upon such factors as the type of the compound, the kind of disease and symptons, it lies in the range of about 1 to about 1,000 mg. more precisely of about 10 to about 1,000 mg. upon oral administration and about 1 to about 300 mg. upon parenteral administration per adult human.

Conventional methods for obtaining dimedone, a typical compound falling within the scope of the general formula (III), can be applied to the production of any compounds (III). Similarly, conventional method for obtaining known compounds falling within the scope of the general formulas (IV) and (V) can be applied to the production of any compounds (IV) and (V). Moreover, the aminomethanol compounds (VI) may be produced by, for example, the method of E. R. Alexander et al, which is described in J. Am. Chem. Soc. 71, 4014 (1949).

For a further explanation of the present inventon, the following Reference and Examples are given, wherein the word "part(s)" is based on weight unless otherwise noted and the relationship between "part(s)" and "volume part(s)" corresponds to that between "gram(s)" and "milliliter(s)".

In the following examples, the recrystallization of the compounds (II) and (I) may be carried out by using suitable organic solvents such as ketones (e.g. acetone, methyl isopropyl ketone, methyl ethyl ketone), alcohols (e.g. ethanol, methanol, isopropanol, propanol, butanol), ethers (e.g. isopropyl ether, tetrahydrofuran, dioxane, methyl ether, ethyl ether), hydrocarbons (e.g. benzene, xylene, toluene), esters (e.g. ethyl acetate, methyl acetate) or suitable mixtures thereof.

REACTION OF STEP (A)

EXAMPLE 1 a. A mixture of 12.75 parts of 2-chloroaniline and 14 parts of dimedone is dissolved in 40 volume parts of ethanol under warming, followed by the addition of 3 drops of glacial acetic acid. The solution is refluxed in a water bath for 2 hours, after which time the ethanol is distilled off and the resulting residue is allowed to cool, whereupon yellow crystals separate. These crystals are collected by filtration, washed with isopropyl ether and recrystallized from acetone. The procedure yields 3-(2-chloroanilino)-5,5-dimethyl-2-cyclohexen-1-one as colorless prisms melting at 150°–152° C.

Elementary analysis: $C_{14}H_{16}NOCl$: Calcd.: C, 67.32; H, 6.45; N, 5.60.
Found: C, 67.13; H, 6.31; N, 5.82.

b. A mixture of 40 parts of dimedone and 36.4 parts of 2-chloroaniline is heated at 170°–175° C for 45 minutes, followed by cooling. The resulting reaction product is recrystallized to obtain yellow cubes. The crystals are collected by filtration, washed well with isopropyl ether and recrystallized from acetone. The procedure yields colorless prisms of 3-(2-chloroanilino)-5,5-dimethyl-2-cyclohexen-1-one. Melting point: 150°–152° C. By procedures similar to those described in Example 1 (a) and (b), the following compounds are produced.

| Starting compound | Product | Melting point (° C) |
|---|---|---|
| Dimedone + 3-Chloroaniline | 3-(3-Chloroanilino)-5,5-dimethyl-2-cyclohexen-1-one | 147–148.5 |
| Dimedone + 4-Chloroaniline | 3-(4-Chloroanilino)-5,5-dimethyl-2-cyclohexen-1-one | 211–212 |
| Dimedone + 3-Methoxyaniline | 3-(3-Methoxyanilino)-5,5-dimethyl-2-cyclohexen-1-one | 118–121 |
| Dimedone + 4-Methoxyaniline | 3-(4-Methoxyanilino)-5,5-dimethyl-2-cyclohexen-1-one | 193 |
| Dimedone + 4-Ethoxyaniline | 3-(4-Ethoxyanilino)-5,5-dimethyl-2-cyclohexen-1-one | 165 |
| 1,3-Cyclohexanedione + 2-Chloroaniline | 3-(2-Chloroaniline)-2-cyclohexen-1-one | 169–170 |
| 1,3-Cyclohexanedione + 3-Chloroaniline | 3-(3-Chloroanilino)-2-cyclohexen-1-one | 158–159 |
| 5-Phenylcyclohexane-1,3-dione + Aqueous solution of ethylamine | 3-Ethylamino-5-phenyl-2-cyclohexen-1-one | 174–175 |
| 5-Phenylcyclohexane-1,3-dione + Phenethylamine | 3-Phenethylamino-5-phenyl-2-cyclohexen-1-one | 168 |
| 5-Phenylcyclohexane-1,3-dione + Cyclohexylamine | 3-Cyclohexylamino-5-phenyl-2-cyclohexen-1-one | 217–218 |
| 5-Phenylcyclohexane-1,3-dione + Aniline | 3-Anilino-5-phenyl-2-cyclohexen-1-one | 242–243 |
| 5-Phenylcyclohexane-1,3-dione + 4-Chloroaniline | 3-(4-Chloroanilino)-5-phenyl-2-cyclohexen-1-one | 241–242 |
| 5-Phenylcyclohexane-1,3-dione + 2-Chloroaniline | 3-(2-Chloroanilino)-5-phenyl-2-cyclohexen-1-one | 174–176 |
| 5-Phenylcyclohexane-1,3-dione + 4-Methoxyaniline | 3-(4-Methoxyanilino)-5-phenyl-2-cyclohexen-1-one | 226–228 |
| 5-Phenylcyclohexane-1,3-dione + 4-Ethoxyaniline | 3-(4-Ethoxyanilino)-5-phenyl-2-cyclohexen-1-one | 203–204 |
| 5-Phenylcyclohexane-1,3-dione + 2-Ethoxyaniline | 3-(2-Ethoxyanilino)-5-phenyl-2-cyclohexen-1-one | 185–186 |
| Cyclohexane-1,3-dione + 4-Chloroaniline | 3-(4-Chloroanilino)-2-cyclohexen-1-one | 192 |
| Cyclohexane-1,3-dione + 4-Hydroxyaniline | 3-(4-Hydroxyanilino)-2-cyclohexen-1-one | 230–233 (decomp.) |
| Cyclohexane-1,3-dione + 3-Methoxyaniline | 3-(3-Methoxyanilino)-2-cyclohexen-1-one | 120 |
| Cyclohexane-1,3-dione + 4-Methoxyaniline | 3-(4-Methoxyanilino)-2-cyclohexen-1-one | 159–160 |
| Cyclohexane-1,3-dione + 2-Ethoxyaniline | 3-(2-Ethoxyanilino)-2-cyclohexen-1-one | 97–98 |
| Cyclohexane-1,3-dione + 3-Ethoxyaniline | 3-(3-Ethoxyanilino)-2-cyclohexen-1-one | 132–133 |
| Cyclohexane-1,3-dione + 3-Methylaniline | 3-(3-Methylanilino)-2-cyclohexen-1-one | 139–141 |
| Cyclohexane-1,3-dione + 4-Methylaniline | 3-(4-Methylanilino)-2-cyclohexen-1-one | 133–134 |
| 5-Methylcyclohexane-1,3-dione + 3-Methoxyaniline | 3-(3-Methoxyanilino)-5-methyl-2-cyclohexen-1-one | 149–150 |
| 5-Methylcyclohexane-1,3-dione + 2-Methylaniline | 3-(2-Methylanilino)-5-methyl-2-cyclohexen-1-one | 175–176 |

REACTION OF STEP (B)

i. Reaction of Step (B)-(i)

EXAMPLE 2

In 10 volume parts of methanol is dissolved 2.15 parts of 3-anilino-5,5-dimethyl-2-cyclohexen-1-one under warming and, then, to the resulting solution 0.9 part of a 37 weight % aqueous solution of formaldehyde, 1.12 part of a 40 weight % aqueous solution of dimethylamine and 1 drop of glacial acetic acid are added. The whole mixture is allowed to stand at room temperature for 1 hour, after which time the methanol is distilled off under reduced pressure. A small amount of isopropanol is added to the resulting residue and the whole mixture is cooled, whereupon colorless crystals separate. The crystals are collected by filtration and recrystallized from isopropyl ether to obtain colorless prisms of 3-anilino-5,5-dimethyl-2-dimethylaminomethyl-2-cyclohexen-1-one. Melting point: 111°–112° C.

Elementary analysis: $C_{17}H_{24}N_2O$: Calcd.: C, 74.95; H, 8.88; N, 10.28. Found: C, 75.28; H, 8.96; N, 10.50.

By procedures similar to those described in Example 2, the following compounds are produced.

| Starting compound | Product | Melting point (° C) |
|---|---|---|
| 3-Anilino-5,5-dimethyl-2-cyclohexen-1-one + diethylamine + formaldehyde | 3-Anilino-5,5-dimethyl-2-diethylaminomethyl-2-cyclohexen-1-one | 110–111 |
| 3-Anilino-5,5-dimethyl-2-cyclohexen-1-one + piperidine + formaldehyde | 3-Anilino-5,5-dimethyl-2-piperidinomethyl-2-cyclohexen-1-one | 134–136 |
| 3-Anilino-5,5-dimethyl-2-cyclohexen-1-one + morpholine + formaldehyde | 3-Anilino-5,5-dimethyl-2-morpholinomethyl-2-cyclohexen-1-one | 161–162 |
| 3-Anilino-5,5-dimethyl-2-cyclohexen-1-one + 4-β-hydroxyethyl-piperazine + formaldehyde | 3-Anilino-5,5-dimethyl-2-(4-β-hydroxyethyl-piperazino)methyl-2-cyclohexen-1-one | 135–136 |

3-(3-Chloroanilino)-5,5-dimethyl-2-piperidinomethyl-2-cyclohexen-1-one. Melting point 123°–124° C 3-(2-Methylanilino)-5-phenyl-2-(3-methylpiperidino)-methyl-2-cyclohexen-1-one. Melting point: 125°–128° C 3-(2-Ethoxyanilino)-5-phenyl-2-(N-methyl-N-benzylamino)-methyl-2-cyclohexen-1-one. Melting point: 144°–145° C 3-(2-Ethoxyanilino)-5-phenyl-2-morpholinomethyl-2-cyclohexen-1-one. Melting point: 160°–162° C 3-(2-Methoxyanilino)-5-phenyl-2-piperidinomethyl-2-cyclohexen-1-one. Melting point: 168°–170° C 3-(2-Methoxyanilino)-5-phenyl-2-morpholinomethyl-2-cyclohexen-1-one. Melting point: 200°–203° C 3-(2-Methoxyanilino)-5-phenyl-2-(N-methyl-N-benzylamino)methyl-2-cyclohexen-1-one. Melting point: 179°–181° C 3-(2-Methoxyanilino)-5-phenyl-2-(4-methylpiperidino)-methyl-2-cyclohexen-1-one. Melting point: 165°–167° C 3-(2-Methoxyanilino)-5-phenyl-2-(3-methylpiperidino)-methyl-2-cyclohexen-1-one. Melting point: 164°–166° C

EXAMPLE 3

2.15 Parts of 3-anilino-5,5-dimethyl-2-cyclohexen-1-one is dissolved in 10 volume parts of methanol under warming and, then, to the resulting solution 0.9 part of a 37 weight % aqueous solution of formaldehyde, 0.81 part of dimethylamine hydrochloride and 1 drop of glacial acetic acid are added. The whole mixture is allowed to stand at room temperature for 1 hour, and after which time, the methanol is distilled off under reduced pressure. To the resulting residue is added, a small amount of isopropyl ether, followed by cooling, whereupon colorless crystals separate. The crystals are collected by filtration and recrystallized from acetone. The procedure yields colorless needles of 3-anilino-5,5-dimethyl-2-dimethylaminomethyl-2-cyclohexen-1-one hydrochloride. Melting point: 169°–170° C Elementary analysis: $C_{17}H_{25}N_2OCl$: Calcd.: C, 66.10; H, 8.15; N, 9.07. Found: C, 66.09; H, 8.21; N, 8.97.

EXAMPLE 4

12.5 Parts of 3-(2-chloroanilino)-5,5-dimethyl-2-cyclohexen-1-one is dissolved in 3o volume parts of methanol under warming and, then, to the resulting solution are added 4.5 parts of a 37 weight % aqueous solution of formaldehyde, 6.05 parts of piperidine hydrochloride and 2 drops of glacial acetic acid. The whole mixture is allowed to stand at room temperature for 1 hour, whereupon a yellow, clear solution is obtained. The methanol is distilled off under reduced pressure, and a small amount of isopropyl ether is added to the resulting residue, followed by cooling, whereupon colorless crystals separate. The crystals are collected by filtration and recrystallized from acetone. The procedure yields colorless prisms of 3-(2-chloroanilino)-5,5-dimethyl-2-piperidinomethyl-2-cyclohexen-1-one hydrochloride. Melting point: 105°–106° C.

Elementary analysis: $C_{20}H_{28}N_2OCL_2 \cdot \frac{1}{2}H_2O$: Calcd.: C, 61.21; H, 7.45; N, 7.14. Found: C, 60.91; H, 7.60; N, 7.25.

By procedures similar to those described in Examples 3 and 4, the following compounds are produced.

| Starting compound | Product | Melting point (° C) |
|---|---|---|
| 3-(2-Chloroanilino)-5,5-dimethyl-2-cyclohexen-1-one + dimethylamine hydrochloride + formaldehyde | 3-(2-Chloroanilino)-5,5-dimethyl-2-dimethylaminomethyl-2-cyclohexen-1-one hydrochloride | 172–173 |
| 3-(4-Chloroanilino)-5,5-dimethyl-2-cyclohexen-1-one + dimethylamine hydrochloride + formaldehyde | 3-(4-Chloroanilino)-5,5-dimethyl-2-dimethylaminomethyl-2-cyclohexen-1-one hydrochloride | 188–205 (decomp.) |
| 3-(4-Chloroanilino)-5,5-dimethyl-2-cyclohexen-1-one + piperidine hydrochloride + formaldehyde | 3-(4-Chloroanilino)-5,5-dimethyl-2-piperidino-methyl-2-cyclohexen-1-one hydrochloride | 142 (decomp.) |
| 3-(3-Methoxyanilino)-5,5-dimethyl-2-cyclohexen-1-one + dimethylamine hydrochloride + formaldehyde | 3-(3-Methoxyanilino)-5,5-dimethyl-2-dimethylaminomethyl-2-cyclohexen-1-one hydrochloride | 115–160 (decomp.) |
| 3-Methylamino-5,5-dimethyl-2-cyclohexen-1-one + piperidine hydrochloride + formaldehyde | 3-Methylamino-5,5-dimethyl-2-piperidinomethyl-2-cyclohexen-1-one hydrochloride | 189 |

-continued

| Starting compound | Product | Melting point (° C) |
|---|---|---|
| 3-(2-Chloroanilino)-2-cyclohexen-1-one + piperidine hydrochloride + formaldehyde | 3-(2-Chloroanilino)-2-piperidinomethyl-2-cyclohexen-1-one hydrochloride | 176–177.5 (decomp.) |
| 3-(4-Methoxyanilino)-5,5-dimethyl-2-cyclohexen-1-one + dimethylamine hydrochloride + formaldehyde | 3-(4-Methoxyanilino)-5,5-dimethyl-2-dimethyl-aminomethyl-2-cyclohexen-1-one hydrochloride | 160–165 |

EXAMPLE 5

2.15 Parts of 3-anilino-5,5-dimethyl-2-cyclohexen-1-one is dissolved in 10 volume parts of methanol under heating and, then, to the resulting solution are added 0.9 part of a 37 weight % aqueous solution of formaldehyde, 0.87 part of morpholine and 1.6 part of 20 weight % hydrochloric acid. The mixture is allowed to stand at room temperture for 1 hour, after which time the methanol is distilled off under reduced pressure, whereupon yellow crystals separate. The crystals are collected by filtration, washed with isopropyl ether and recrystallized from acetone. The procedure yields colorless scales of 3-anilino-5,5-dimethyl-2-morpholinomethyl-2-cyclohexen-1- one hydrochloride. Melting point: 172°–173° C Elementary analysis: $C_{19}H_{27}N_2O_2Cl \cdot H_2O$:Calcd: C, 61.85; H, 7.92; N, 7.59. Found: C, 61.88; H, 7.87; N, 7.67.

EXAMPLE 6

2.15 Parts of 3-anilino-5,5-dimethyl-2-cyclohexen-1-one is dissolved in 10 volume parts of methanol under warming and, then, to the resulting solution are added 0.9 part of a 37 weight % aqueous solution of formaldehyde, 1.3 parts of N-(β-hydroxyethyl) piperazine and 1.6 parts of 20 weight % hydrochloric acid. The whole mixture is allowed to stand at room temperature for 1 hour. After which time, the methanol is distilled off under reduced pressure, and isopropyl ether is added to the resulting residue, followed by cooling, whereupon pale yellow crystals separate. The crystals are collected by filtration and recrystallized from acetone. The procedure yields colorless powdery crystals of 3-anilino-2-(4-β-hydroxypiperazino)methyl-2-cyclohexen-1-one hydrochloride.

Melting point: 172°–173° C

Elementary analysis: $C_{21}H_{32}N_3O_2Cl$: Calcd.: C, 64.02; H, 8.18; N, 10.66. Found: C, 64.18; H, 8.28; N, 10.95.

ii. Reaction of Step (B)-(ii)

EXAMPLE 7

In 20 volume parts of methanol is dissolved 4.3 parts of 3-anilino-5,5-dimethyl-2-cyclohexen-1-one, followed by the addition of 2.3 parts of dimethylaminomethanol. The resulting mixture is allowed to stand at room temperature for 1 hour, after which time the methanol is distilled off under reduced pressure. The resulting residue is caused to crystallize by the addition of isopropyl ether. The isopropyl ether-soluble fraction is separated from the insolubles, and the soluble fraction is concentrated to recover a crude product of 3-anilino-5,5-dimethyl-2-dimethylaminomethyl-2-cyclohexen-1-one. The resulting crude product is recrystallized from isopropyl ether to yield colorless prisms melting at 118°–119° C.

Elementary analysis: $C_{17}H_{24}N_2O$: Calcd.: C, 74.95; H, 8.88; N, 10.28. Found: C, 75.12; H, 8.98; N, 10.16.

By procedures similar to those described in Example 7, the following compounds are produced from the corresponding aminocyclohexenone compounds (II) and aminomethanol compounds (VI).

3-Anilino-5,5-dimethyl-2-diethylaminomethyl-2-cyclohexen-1-one. Melting point: 110°–111° C 3-Anilino-5,5-dimethyl-2-piperidinomethyl-2-cyclohexen-1-one. Melting point: 134°–136° C 3-Anilino-5,5-dimethyl-2-morpholinomethyl-2-cyclohexen-1-one. Melting point: 161°–162° C 3-Anilino-5,5-dimethyl-2-(4-β-hydroxyethyl-piperazino)methyl-2-cylcohexen-1-one. Melting point: 135°–136° C 3-(3-Chloroanilino)-5,5-dimethyl-2-piperidinomethyl-2-cyclohexen-1-one. Melting point: 123°–124° C 3-(2-Methylanilino)-5-phenyl-2-(3-methylpiperidino)-methyl-2-cyclohexen-1-one. Melting point 125°–128° C 3-(2-Ethoxyanilino)-5-phenyl-2-(N-methyl-N-benzylamino)methyl-2-cyclohexen-1-one. Melting point: 144°–145° C 3-(2-Ethoxyanilino)-5-phenyl-2-morpholinomethyl-2-cyclohexen-1-one. Melting point: 160°–162° C 3-(2-Methoxyanilino)-5-phenyl-2-piperidinomethyl-2-cyclohexen-1-one. Melting point: 168°–170° C 3-(2-Methoxyanilino)-5-phenyl-2-morpholinomethyl-2-cyclohexen-1-one. Melting point: 200°–203° C 3-(2-Methoxyanilino)-5-phenyl-2-(N-methyl-N-benzylamino)-methyl-2-cyclohexen-1-one. Melting point: 179°–181° C 3-(2-Methoxyanilino)-5-phenyl-2-(4-methylpiperidino)-methyl-2-cyclohexen-1-one. Melting point: 165°–167° C 3-(2-Methoxyanilino)-5-phenyl-2-(3-methylpiperidino)-methyl-2-cyclohexen-1-one. Melting point: 164°–166° C

EXAMPLE 8

In 20 volume parts of methanol is dissolved 4.6 parts of 3-(4-ethoxyanilino)-2-cyclohexen-1-one, followed by the addition of 3.2 parts of diethylaminomethanol. The resulting mixture is allowed to stand at room temperature for 2 hours, after which time the methanol is distilled off. To the residue is added isopropyl ether and the resulting resinous precipitate is filtered off. The filtrate is concentrated, and to the resultant 6.6 volume parts of 10 % ethanolic hydrochloric acid is added, followed by further concentration. Ethyl acetate is added to the resulting concentrate and the separated crystals are collected by filtration. Recrystallization from a mixture of ethyl acetate and methanol yields colorless prisms of 3-(4-ethoxyanilino)-2-diethylaminomethyl-2-cyclohexen-1-one hydrochloride melting at 127°–130° C (decomp.).

Elementary analysis: $C_{19}H_{28}N_2O_2O_2 \cdot HCl$: Calcd.: C, 64.67; H, 8.28; N, 7.94. Found: C, 64.69; H, 8.50; N, 8.11.

By procedures similar to those described in Examples 3 to 6 [(i.e. by the reaction of Step (B)-(i)] or in Examples 7 to 8 [i.e. by the reaction of Step (B) (ii)], the following compounds are produced from the corresponding aminocyclohexenone compounds (II), the amine compounds (V) and formaldehyde, or from the corresponding aminocyclohexenone compounds (II) and aminomethanol compound (VI).

| Compound | Reaction(s) by which the compound is produced |
|---|---|
| 3-Anilino-5,5-dimethyl-2-dimethylaminomethyl-2-cyclohexen-1-one hydrochloride. Melting point: 169–170° C | Reaction of Step(B)-(ii) |
| 3-Anilino-5,5-dimethyl-2-morpholinomethyl-2-cyclohexen-1-one hydrochloride. Melting point: 172–173° C(decomp.) | Reaction of Step(B)-(ii) |
| 3-Anilino-5,5-dimethyl-2-(4-β-hydroxyethylpiperazino)methyl-2-cyclohexen-1-one hydrochloride. Melting point: 172–173° C | Reaction of Step(B)-(ii) |
| 3-(2-Chloroanilino)-5,5-dimethyl-2-dimethylaminomethyl-2-cyclohexen-1-one hydrochloride. Melting point: 172–173° C | Reaction of Step(B)-(ii) |
| 3-(2-Chloroanilino)-5,5-dimethyl-2-piperidinomethyl-2-cyclohexen-1-one hydrochloride. Melting point: 105–106° C | Reaction of Step(B)-(ii) |
| 3-(2-Chloroanilino)-5,5-dimethyl-2-morpholinomethyl-2-cyclohexen-1-one hydrochloride. Melting point: 189° C(decomp.) | Reactions of Step(B)-(i) and (ii) |
| 3-(2-Chloroanilino)-5,5-dimethyl-2-(4-β-hydroxyethylpiperazino)methyl-2-cyclohexen-1-one hydrochloride ½ hydrate. Melting point: 131° C | Reactions of Step(B)-(i) and (ii) |
| 3-(3-Chloroanilino)-5,5-dimethyl-2-dimethylaminomethyl-2-cyclohexen-1-one-hydrochloride. Melting point: 176° C | Reactions of Step(B)-(i) and (ii) |
| 3-(3-Chloroanilino)-5,5-dimethyl-2-diethylaminomethyl-2-cyclohexen-1-one-hydrochloride. Melting point: 140° C | Reactions of Step(B)-(i) and (ii) |
| 3-(3-Chloroanilino)-5,5-dimethyl-2-morpholinomethyl-2-cyclohexen-1-one hydrochloride. Melting point: 182–183.5° C(decomp.) | Reactions of Step(B)-(i) and (ii) |
| 3-(4-Chloroanilino)-5,5-dimethyl-2-dimethylaminomethyl-2-cyclohexen-1-one hydrochloride. Melting point: 188–205° C(decomp.) | Reaction of Step(B)-(ii) |
| 3-(4-Chloroanilino)-5,5-dimethyl-2-diethylaminomethyl-2-cyclohexen-1-one hydrochloride ½ hydrate. Melting point: 141° C(decomp.) | Reactions of Step(B)-(i) and (ii) |
| 3-(4-Chloroanilino)-5,5-dimethyl-2-piperidinomethyl-2-cyclohexen-1-one hydrochloride. Melting point: 142° C(decomp.) | Reaction of Step(B)-(ii) |
| 3-(4-Chloroanilino)-5,5-dimethyl-2-morpholinomethyl-2-cyclohexen-1-one hydrochloride hydrate. Melting point: 141° C(decomp.) | Reactions of Step(B)-(i) and (ii) |
| 3-(4-Chloroanilino)-5,5-dimethyl-2-(N-methyl-N-benzylamino)methyl-2-cyclohexen-1-one hydrochloride. Melting point: 186° C(decomp.) | Reactions of Step(B)-(i) and (ii) |
| 3-(2-Hydroxyanilino)-5,5-dimethyl-2-dimethylaminomethyl-2-cyclohexen-1-one hydrochloride. Melting point: 177–178° C(decomp.) | Reactions of Step(B)-(i) and (ii) |
| 3-(3-Methoxyanilino)-5,5-dimethyl-2-dimethylaminomethyl-2-cyclohexen-1-one hydrochloride. Melting point: 160–165° C(decomp.) | Reaction of Step(B)-(ii) |
| 3-(2-Methoxyanilino)-5,5-dimethyl-2-piperidinomethyl-2-cyclohexen-1-one hydrochloride. Melting point: 162–164° C(decomp.) | Reactions of Step(B)-(i) and (ii) |
| 3-(3-Methoxyanilino)-5,5-dimethyl-2-diethylaminomethyl-2-cyclohexen-1-one hydrochloride. Melting point: 129–132° C(decomp.) | Reactions of Step(B)-(i) and (ii) |
| 3-(3-Methoxyanilino)-5,5-dimethyl-2-piperidinomethyl-2-cyclohexen-1-one hydrochloride hydrate. Melting point: 107–109° C | Reactions of Step(B)-(i) and (ii) |
| 3-(3-Methoxyanilino)-5,5-dimethyl-2-morpholinomethyl-2-cyclohexen-1-one hydrochloride hydrate. Melting point: 134–137° C | Reactions of Step(B)-(i) and (ii) |
| 3-(3-Methoxyanilino)-5,5-dimethyl-2-(N-methyl-N-benzylamino)methyl-2-cyclohexen-1-one hydrochloride. Melting point: 160–161° C(decomp.) | Reactions of Step(B)-(i) and (ii) |
| 3-(3-Methoxyanilino)-5,5-dimethyl-2-(N-methyl-N-phenethylamino)methyl-2-cyclohexen-1-one hydrochloride. Melting point: 112–118° C(decomp.) | Reactions of Step(B)-(i) and (ii) |
| 3-(4-Methoxyanilino)-5,5-dimethyl-2-dimethylaminomethyl-2-cyclohexen-1-one hydrochloride. Melting point: 160–165° C | Reaction of Step(B)-(ii) |
| 3-(4-Methoxyanilino)-5,5-dimethyl-2-piperidinomethyl-2-cyclohexen-1-one hydrochloride hydrate. Melting point: 110–117° C | Reactions of Step(B)-(i) and (ii) |
| 3-(4-Methoxyanilino)-5,5-dimethyl-2-morpholinomethyl-2-cyclohexen-1-one hydrochloride ½ hydrate. Melting point: 134–137° C | Reactions of Step(B)-(i) and (ii) |
| 3-(2-Ethoxyanilino)-5,5-dimethyl-2-piperidinomethyl-2-cyclohexen-1-one hydrochloride hydrate. Melting point: 147–149° C(decomp.) | Reactions of Step(B)-(i) and (ii) |
| 3-(4-Ethoxyanilino)-5,5-dimethyl-2-dimethylaminomethyl-2-cyclohexen-1-one hydrochloride. Melting point: 179–180° C | Reactions of Step(B)-(i) and (ii) |
| 3-(4-Ethoxyanilino)-5,5-dimethyl-2-morpholinomethyl-2-cyclohexen-1-one hydrochloride. Melting point: 185° C | Reactions of Step(B)-(i) and (ii) |
| 3-(4-Ethoxyanilino)-5,5-dimethyl-2-(N-methyl-N-benzylamino)methyl-2-cyclohexen-1-one hydrochloride. Melting point: 152–157° C(decomp.) | Reactions of Step(B)-(i) and (ii) |
| 3-(4-Ethoxyanilino)-5,5-dimethyl-2-(N-methyl-N-phenethylamino)methyl-2-cyclohexen-1-one hydrochloride hydrate. Melting point: 160–165° C | Reactions of Step(B)-(i) and (ii) |
| 3-(2-Methylanilino)-5,5-dimethyl-2-piperidinomethyl-2-cyclohexen-1-one hydrochloride ½ hydrate. Melting point: 167–168° C(decomp.) | Reactions of Step(B)-(i) and (ii) |
| 3-Methylamino-5,5-dimethyl-2-dimethylaminomethyl-2-cyclohexen-1-one hydrochloride ½ hydrate. Melting point: 186° C | Reactions of Step(B)-(i) and (ii) |
| 3-Methylamino-5,5-dimethyl-2-diethylaminomethyl-2-cyclohexen-1-one hydrochloride. Melting point: 191° C | Reactions of Step(B)-(i) and (ii) |
| 3-Methylamino-5,5-dimethyl-2-piperidinomethyl-2-cyclohexen-1-one hydrochloride. Melting point: 189° C | Reaction of Step(B)-(ii) |
| 3-Methylamino-5,5-dimethyl-2-morpholinomethyl-2-cyclohexen-1-one hydrochloride hydrate. Melting point: 178° C | Reactions of Step(B)-(i) and (ii) |
| 3-Anilino-2-dimethylaminomethyl-2-cyclohexen-1-one hydrochloride. Melting point: 140–143° C(decomp.) | Reactions of Step(B)-(i) and (ii) |
| 3-Anilino-2-diethylaminomethyl-2-cyclohexen-1-one hydrochloride. Melting point: 128–131° C(decomp.) | Reactions of Step(B)-(i) and (ii) |
| 3-Anilino-2-piperidinomethyl-2-cyclohexen-1-one hydrochloride. Melting point: 163–166° C(decomp.) | Reactions of Step(B)-(i) and (ii) |
| 3-Anilino-2-morpholinomethyl-2-cyclohexen-1-one hydrochloride. Melting point: 141–143° C(decomp.) | Reactions of Step(B)-(i) and (ii) |
| 3-(2-Chloroanilino)-2-dimethylaminomethyl-2-cyclohexen-1-one hydrochloride. Melting point: 142–144° C(decomp.) | Reactions of Step(B)-(i) and (ii) |
| 3-(2-Chloroanilino)-2-piperidinomethyl-2-cyclohexen-1-one hydrochloride. Melting point: 176–177.5° C | Reaction of Step(B)-(ii) |
| 3-(2-Chloroanilino)-2-morpholinomethyl-2-cyclohexen-1-one hydrochloride. Melting point: 164–165° C(decomp.) | Reactions of Step(B)-(i) and (ii) |
| 3-(2-Chloroanilino)-2-(4-β-hydroxyethylpiperazino)methyl-2-cyclohexen-1-one hydrochloride. Melting point: 165–167° C(decomp.) | Reactions of Step(B)-(i) and (ii) |
| 3-(2-Chloroanilino)-2-(N-methyl-N-benzylamino)methyl-2-cyclohexen-1-one hydrochloride. Melting point: 152–153° C(decomp.) | Reactions of Step(B)-(i) and (ii) |
| 3-(2-Chloroanilino)-2-(4-methylpiperazino)methyl-2-cyclohexen-1-one | Reactions of Step(B)-(i) |

| Compound | Reaction(s) by which the compound is produced |
|---|---|
| one hydrochloride. Melting point: 173-175° C(decomp.) | and (ii) |
| 3-(2-Chloroanilino)-2-(4-methyl-piperidino)methyl-2-cyclohexen-1-one hydrochloride. Melting point: 163-165° C | Reactions of Step(B)-(i) and (ii) |
| 3-(3-Chloroanilino)-2-dimethylamino methyl-2-cyclohexen-1-one hydrochloride. Melting point: 162° C(decomp.) | Reactions of Step(B)-(i) and (ii) |
| 3-(3-Chloroanilino)-2-piperidinomethyl-2-cyclohexen-1-one hydrochloride. Melting point: 184° C(decomp.) | Reactions of Step(B)-(i) and (ii) |
| 3-(3-Chloroanilino)-2-morpholinomethyl-2-cyclohexen-1-one hydrochloride. Melting point: 172° C(decomp.) | Reactions of Step(B)-(i) and (ii) |
| 3-(3-Chloroanilino)-2-(4-β-hydroxyethyl-piperazino)methyl-2-cyclohexen-1-one hydrochloride. Melting point: 173° C(decomp.) | Reactions of Step(B)-(i) and (ii) |
| 3-(4-Chloroanilino)-2-dimethylamino-methyl-2-cyclohexen-1-one hydrochloride. Melting point: 167° C(decomp.) | Reactions of Step(B)-(i) and (ii) |
| 3-(4-Chloroanilino)-2-piperidinomethyl-2-cyclohexen-1-one hydrochloride ½ hydrate. Melting point: 135-136° C(decomp.) | Reactions of Step(B)-(i) and (ii) |
| 3-(4-Chloroanilino)-2-morpholinomethyl-2-cyclohexen-1-one hydrochloride. Melting point: 170-172° C(decomp.) | Reactions of Step(B)-(i) and (ii) |
| 3-(4-Chloroanilino)-2-(4-β-hydroxy-ethylpiperazino)methyl-2-cyclohexen-1-one hydrochloride. Melting point: 184-185° C(decomp.) | Reactions of Step(B)-(i) and (ii) |
| 3-(4-Chloroanilino)-2-(N-methyl-N-benzylamino)methyl-2-cyclohexen-1-one hydrochloride. Melting point: 149-150° C(decomp.) | Reactions of Step(B)-(i) and (ii) |
| 3-(4-Hydroxyanilino)-2-dimethylamino-methyl-2-cyclohexen-1-one hydrochloride ½ hydrate. Melting point: 170-173° C(decomp.) | Reactions of Step(B)-(i) and (ii) |
| 3-(4-Hydroxyanilino)-2-dimethylamino-methyl-2-cyclohexen-1-one hydrochloride. Melting point: 166-169° C(decomp.) | Reactions of Step(B)-(i) and (ii) |
| 3-(4-Hydroxyanilino)-2-piperidinomethyl-2-cyclohexen-1-one hydrochloride. Melting point: 177-180° C(decomp.) | Reactions of Step(B)-(i) and (ii) |
| 3-(4-Hydroxyanilino)-2-(N-methyl-N-benzylamino)methyl-2-cyclohexen-1-one hydrochloride. Melting point: 154-156° C(decomp.) | Reactions of Step(B)-(i) and (ii) |
| 3-(2-Methoxyanilino)-2-dimethylamino-methyl-2-cyclohexen-1-one hydrochloride. Melting point: 166° C(decomp.) | Reactions of Step(B)-(i) and (ii) |
| 3-(2-Methoxyanilino)-2-piperidinomethyl-2-cyclohexen-1-one hydrochloride ¼ hydrate. Melting point: 187-188° C(decomp.) | Reactions of Step(B)-(i) and (ii) |
| 3-(2-Methoxyanilino)-2-morpholinomethyl-2-cyclohexen-1-one hydrochloride ½ hydrate. Melting point: 176° C(decomp.) | Reactions of Step (B)-(i) |
| 3-(2-Methoxyanilino)-2-(4-β-hydroxy-ethylpiperazino)methyl-2-cyclohexene-1-one hydrochloride. Melting point: 169-170° C)decomp.) | Reactions of Step(B)-(i) and (ii) |
| 3-(2-Methoxyanilino)-2-(N-methyl-N-benzylamino)methyl-2-cyclohexen-1-one hydrochloride ¼ hydrate. Melting point: 160-161° C(decomp.) | Reactions of Step(B)-(i) and (ii) |
| 3-(3-Methoxyanilino)-2-dimethylamino-methyl-2-cyclohexen-1-one hydrochloride. Melting point: 120-121° C(decomp.) | Reactions of Step(B)-(i) and (ii) |
| 3-(3-Methoxyanilino)-2-piperidinomethyl-2-cyclohexen-1-one hydrochloride. Melting point: 148-151° C(decomp.) | Reactions of Step (B)-(i) and (ii) |
| 3-(3-Methoxyanilino)-2-morpholinomethyl-2-cyclohexen-1-one hydrochloride. Melting point: 147° C(decomp.) | Reactions of Step(B)-(i) and (ii) |
| 3-(3-Methoxyanilino)-2-(4-β-hydroxy-ethylpiperazino)methyl-2-cyclohexen-1-one hydrochloride. Melting point: 141-143° C(decomo.) | Reactions of Step(B)-(i) and (ii) |
| 3-(3-Methoxyanilino)-2-(4-methyl-piperazino)methyl-2-cyclohexen-1-one hydrochloride ½ hydrate. Melting point: 152-152° C(decomp.) | Reactions of Step(B)-(i) and (ii) |
| 3-(3-Methoxyanilino)-2-(4-methyl-piperidino)methyl-2-cyclohexen-1-one hydrochloride. Melting point: 150-151° C(decomp.) | Reactions of Step(B)-(i) and (ii) |
| 3-(4-Methoxyanilino)-2-dimethylamino-methyl-2-cyclohexen-1-one hydrochloride. Melting point: 166-167° C(decomp.) | Reactions of Step(B)-(i) and (ii) |
| 3-(4-Methoxyanilino)-2-diethylamino-methyl-2-cyclohexen-1-one hydrochloride ½ hydrate. Melting point: 95-96° C(decomp.) | Reactions of Step(B)-(i) and (ii) |
| 3-(4-Methoxyanilino)-2-piperidino-methyl-2-cyclohexen-1-one hydrochloride. Melting point: 170-171° C(decomp.) | Reactions of Step(B)-(i) and (ii) |
| 3-(4-Methoxyanilino)-2-morpholino-methyl-2-cyclohexen-1-one hydrochloride. Melting point: 168-169° C(decomp.) | Reactions of Step(B)-(i) |
| 3-(4-Methoxyanilino)-2-(4-β-hydroxy-ethylpiperazino)methyl-2-cyclohexen-1-one hydrochloride. and (ii) Melting point: 175-176° C(decomp.) | Reactions of Step(B)-(i) and (ii) |
| 3-(4-Methoxyanilino)-2-(N-methyl-N-benzylamino)methyl-2-cyclohexen-1-one hydrochloride. Melting point: 78-81° C(decomp.) | Reactions of Step(B)-(i) and (ii) |
| 3-(4-Methoxyanilino)-2-(4-methyl-piperazino)methyl-2-cyclohexen-1-one hydrochloride. Melting point: 156-157° C(decomp.) | Reactions of Step(B)-(i) and (ii) |
| 3-(4-Methoxyanilino)-2-(2-methyl-piperidino)methyl-2-cyclohexen-1-one hydrochloride. Melting point: 120-121° C(decomp.) | Reactions of Step(B)-(i) and (ii) |
| 3-(4-Methoxyanilino)-2-(4-methyl-piperidino)methyl-2-cyclohexen-1-one hydrochloride ½hydrate. Melting point: 105-106° C(decomp.) | Reactions of Step(B)-(i) and (ii) |
| 3-(4-Methoxyanilino)-2-(3-methyl-piperidino)methyl-2-cyclohexen-1-one hydrochloride ½ hydrate. Melting point: 131-132° C(decomp.) | Reactions of Step(B)-(i) and (ii) |
| 3-(2-Ethoxyanilino)-2-dimethylamino-methyl-2-cyclohexen-1-one hydrochloride. Melting point: 149-151° C(decomp.) | Reactions of Step(B)-(i) and (ii) |
| 3-(2-Ethoxyanilino)-2-piperidino-methyl-2-cyclohexen-1-one hydrochloride hydrate. Melting point: 110-112° C(decomp.) | Reactions of Step(B)-(i) and (ii) |
| 3-(2-Ethoxyanilino)-2-morpholinomethyl-2-cyclohexen-1-one hydrochloride. Melting point: 143-145° C(decomp.) | Reactions of Step(B)-(i) and (ii) |
| 3-(2-Ethoxyanilino)-2-(4-β-hydroxy-ethylpiperazino)methyl-2-cyclohexen-1-one hydrochloride. Melting point: 168-169° C(decomp.) | Reactions of Step(B)-(i) and (ii) |
| 3-(3-Ethoxyanilino)-2-dimethylamino-methyl-2-cyclohexen-1-one hydrochloride hydrate. Melting point: 108-110° C(decomp.) | Reactions of Step(B)-(i) and (ii) |
| 3-(3-Ethoxyanilino)-2-diethylamino-methyl-2-cyclohexen-1-one hydrochloride. Melting point: 140-142° C(decomp.) | Reactions of Step(B)-(i) and (ii) |
| 3-(3-Ethoxyanilino)-2-piperidinomethyl-2-cyclohexen-1-one hydrochloride. Melting point: 134-136° C(decomp.) | Reactions of Step(B)-(i) and (ii) |
| 3-(3-Ethoxyanilino)-2-morpholinomethyl-2-cyclohexen-1-one hydrochloride. Melting point: 145-148° C(decomp.) | Reactions of Step(B)-(i) and (ii) |
| 3-(3-Ethoxyanilino)-2-(N-methyl-N-benzylamino)methyl-2-cyclohexen-1-one hydrochloride. Melting point: 144-146° C(decomp.) | Reactions of Step(B)-(i) and (ii) |
| 3-(3-Ethoxyanilino)-2-(4-methyl-piperazino)methyl-2-cyclohexen-1-one hydrochloride ½ hydrate. Melting point: 153-155° C(decomp.) | Reactions of Step(B)-(i) and (ii) |
| 3-(3-Ethoxyanilino)-2-(4-methyl-piperidino)methyl-2-cyclohexen-1-one hydrochloride. Melting point: 154-155° C(decomp.) | Reactions of Step(B)-(i) and (ii) |
| 3-(4-Ethoxyanilino)-2-dimethylamino- | Reactions of |

| Compound | Reaction(s) by which the compound is produced |
|---|---|
| methyl-2-cyclohexen-1-one hydrochloride. Melting point: 109–111° C(decomp.) | Step(B)-(i) and (ii) |
| 3-(4-Ethoxyanilino)-2-diethylaminomethyl-2-cyclohexen-1-one hydrochloride. Melting point: 127–130° C(decomp.) | Reactions of Step(B)-(i) and (ii) |
| 3-(4-Ethoxyanilino)-2-piperidinomethyl-2-cyclohexen-1-one hydrochloride. Melting point: 145–147° C(decomp.) | Reactions of Step(B)-(i) and (ii) |
| 3-(4-Ethoxyanilino)-2-morpholinomethyl-2-cyclohexen-1-one hydrochloride. Melting point: 130–132° C(decomp.) | Reactions of Step(B)-(i) and (ii) |
| 3-(4-Ethoxyanilino)-2-(4-β-hydroxyethylpiperazino)methyl-2-cyclohexen-1-one hydrochloride. Melting point: 160–161° C(decomp.) | Reactions of Step(B)-(i) and (ii) |
| 3-(4-Ethoxyanilino)-2-(N-methyl-N-benzylamino)methyl-2-cyclohexen-1-one hydrochloride. Melting point: 134–135° C(decomp). | Reactions of Step(B)-(i) and (ii) |
| 3-(4-Ethoxyanilino)-2-(2-methylpiperidino)methyl-2-cyclohexen-1-one hydrochloride. Melting point: 130–133° C(decomp). | Reactions of Step(B)-(i) and (ii) |
| 3-(2-Methylanilino)-2-dimethylaminomethyl-2-cyclohexen-1-one hydrochloride. Melting point: 157–158° C(decomp.) | Reactions of Step(B)-(i) and (ii) |
| 3-(2-Methylanilino)-2-piperidinomethyl-2-cyclohexen-1-one hydrochloride. Melting point: 164–165° C(decomp.) | Reactions of Step(B)-(i) and (ii) |
| 3-(2-Methylanilino)-2-morpholinomethyl-2-cyclohexen-1-one hydrochloride. Melting point: 154–155° C(decomp.) | Reactions of Step(B)-(i) and (ii) |
| 3-(2-Methylanilino)-2-(4-β-hydroxyethylpiperazino)methyl-2-cyclohexen-1-one hydrochloride. Melting point: 170–171° C(decomp.) | Reactions of Step(B)-(i) and (ii) |
| 3-(2-Methylanilino)-2-(4-methylpiperidino)methyl-2-cyclohexen-1-one hydrochloride. Melting point: 160–161.5° C(decomp.) | Reactions of Step(B)-(i) and (ii) |
| 3-(3-Methylanilino)-2-dimethylaminomethyl-2-cyclohexen-1-one hydrochloride. Melting point: 133–135° C(decomp.) | Reactions of Step(B)-(i) and (ii) |
| 3-(3-Methylanilino)-2-piperidinomethyl-2-cyclohexen-1-one hydrochloride. Melting point: 142–144° C(decomp.) | Reactions of Step(B)-(i) and (ii) |
| 3-(3-Methylanilino)-2-morpholinomethyl-2-cyclohexen-1-one hydrochloride. Melting point: 164–165° C(decomp.) | Reactions of Step(B)-(i) and (ii) |
| 3-(3-Methylanilino)-2-(4-β-hydroxyethylpiperazino)methyl-2-cyclohexen-1-one hydrochloride. Melting point: 162–163° C(decomp.) | Reactions of Step(B)-(i) and (ii) |
| 3-(3-Methylanilino)-2-(N-methyl-N-benzylamino)methyl-2-cyclohexen-1-one hydrochloride. Melting point: 132–133° C(decomp.) | Reactions of Step(B)-(i) and (ii) |
| 3-(4-Methylanilino)-2-dimethylaminomethyl-2-cyclohexen-1-one hydrochloride. Melting point: 190–192° C(decomp.) | Reactions of Step(B)-(i) and (ii) |
| 3-(4-Methylanilino)-2-piperidinomethyl-2-cyclohexen-1-one hydrochloride. Melting point: 140–141° C(decomp.) | Reactions of Step(B)-(i) and (ii) |
| 3-(4-Methylanilino)-2-morpholinomethyl-2-cyclohexen-1-one hydrochloride. Melting point: 162–164° C(decomp.) | Reactions of Step(B)-(i) and (ii) |
| 3-(4-Methylanilino)-2-(4-methylpiperazino)methyl-2-cyclohexen-1-one hydrochloride. Melting point: 182–185° C(decomp.) | Reactions of Step(B)-(i) and (ii) |
| 3-Benzylamino-2-dimethylaminomethyl-2-cyclohexen-1-one hydrochloride. Melting point: 169–170° C(decomp.) | Reactions of Step(b)-(i) and (ii) |
| 3-Benzylamino-2-piperidinomethyl-2-cyclohexen-1-one hydrochloride. Melting point: 174° C(decomp.) | Reactions of Step(B)-(i) and (ii) |
| 3-Benzylamino-2-morpholinomethyl-2-cyclohexen-1-one hydrochloride. Melting point: 167° C(decomp.) | Reactions of Step(B)-(i) and (ii) |
| 3-Benzylamino-2-(N-methyl-N-benzylamino)methyl-2-cyclohexen-1-one hydrochloride. Melting point: 164–165° C(decomp.) | Reactions of Step(B)-(i) and (ii) |
| 3-Isopropylamino-2-piperidinomethyl-2-cyclohexen-1-one hydrochloride ½ hydrate. Melting point: 152–154° C(decomp.) | Reactions of Step(B)-(i) and (ii) |
| 3-Phenylthylamino-2-dimethylaminomethyl-2-cyclohexen-1-one hydrochloride. Melting point: 134–137° C(decomp.) | Reactions of Step(B)-(i) and (ii) |
| 3-Phenethylamino-2-piperidinomethyl-2-cyclohexen-1-one dihydrochloride. Melting point: 122–124° C(decomp.) | Reactions of Step(B)-(i) and (ii) |
| 3-Phenethylamino-2-morpholinomethyl-2-cyclohexen-1-one hydrochloride. Melting point: 112–115° C(decomp.) | Reactions of Step(B)-(i) and (ii) |
| 3-Cyclohexylamino-2-dimethylaminomethyl-2-cyclohexen-1-one hydrochloride. Melting point: 169–171° C(decomp.) | Reactions of Step(B)-(i) and (ii) |
| 3-Cyclohexylamino-2-piperidinomethyl-2-cyclohexen-1-one hydrochloride. Melting point: 150–152° C(decomp.) | Reactions of Step(B)-(i) and (ii) |
| 3-(3-Dimethylaminopropylamino)-2-dimethylaminomethyl-2-cyclohexen-1-one dihydrochloride. Melting point: 155–158° C(decomp.) | Reactions of Step(B)-(i) and (ii) |
| 3-(3-Dimethylaminopropylamino)-2-piperidinomethyl-2-cyclohexen-1-one dihydrochloride. Melting point: 163–165° C(decomp.) | Reactions of Step(B)-(i) and (ii) |
| 3-(3-Dimethylaminopropylamino)-2-morpholinomethyl-2-cyclohexen-1-one dihydrochloride. Melting point: 160–162° C(decomp.) | Reactions of Step(B)-(i) and (ii) |
| 3-(2-Chloroanilino)-5-methyl-2-piperidinomethyl-2-cyclohexen-1-one hydrochloride. Melting point: 167–168° C(decomp.) | Reactions of Step(B)-(i) and (ii) |
| 3-(2-Chloroanilino)-5-methyl-2-(4-methylpiperazino)methyl-2-cyclohexen-1-one hydrochloride hydrate. Melting point: 175–177° C(decomp.) | Reactions of Step(B)-(i) and (ii) |
| 3-(2-Chloroanilino)-5-methyl-2-(4-methylpiperazino)methyl-2-cyclohexen-1-one hydrochloride. Melting point: 135–136° C | Reactions of Step(B)-(i) and (ii) |
| 3-(2-Methoxyanilino)-5-methyl-2-piperidinomethyl-2-cyclohexen-1-one hydrochloride ½ hydrate. Melting point: 142–143° C(decomp.) | Reactions of Step(B)-(i) and (ii) |
| 3-(3-Methoxyanilino)-5-methyl-2-dimethylaminomethyl-2-cyclohexen-1-one hydrochloride. Melting point: 167–169° C(decomp.) | Reactions of Step(B)-(i) and (ii) |
| 3-(3-Methoxyanilino)-5-methyl-2-diethylaminomethyl-2-cyclohexen-1-one hydrochloride. Melting point: 145–147° C(decomp.) | Reactions of Step(B)-(i) and (ii) |
| 3-(3-Methoxyanilino)-5-methyl-2-piperidinomethyl-2-cyclohexen-1-one hydrochloride. Melting point: 160–163° C(decomp.) | Reactions of Step(B)-(i) and (ii) |
| 3-(3-Methoxyanilino)-5-methyl-2-morpholinomethyl-2-cyclohexen-1-one hydrochloride ½ hydrate. Melting point: 124–125° C(decomp.) | Reactions of Step(B)-(i) and (ii) |
| 3-(3-Methoxyanilino)-5-methyl-2-(N-methyl-N-benzylamino)methyl-2-cyclohexen-1-one hydrochloride. Melting point: 153–154° C(decomp.) | Reactions of Step(B)-(i) and (ii) |
| 3-(2-Ethoxyanilino)-5-methyl-2-piperidinomethyl-2-cyclohexen-1-one hydrochloride. Melting point: 164–166° C(decomp.) | Reactions of Step(B)-(i) and (ii) |
| 3-(2-Methylanilino)-5-methyl-2-piperidinomethyl-2-cyclohexen-1-one hydrochloride. Melting point: 162–164° C(decomp.) | Reactions of Step(B)-(i) and (ii) |
| 3-Anilino-5-phenyl-2-dimethylaminomethyl-2-cyclohexen-1-one hydrochloride ½ hydrate. Melting point: 144–145° C | Reactions of Step(B)-(i) and (ii) |
| 3-Anilino-5-phenyl-2-diethylaminomethyl-2-cyclohexen-1-one hydrochloride hydrate. Melting point: 113–114° C | Reactions of Step(B)-(i) and (ii) |
| 3-Anilino-5-phenyl-2-piperidinomethyl-2-cyclohexen-1-one hydrochloride ½ hydrate. Melting point: 139–140° C | Reactions of Step(B)-(i) and (ii) |
| 3-Anilino-5-phenyl-2-morpholinomethyl-2-cyclohexen-1-one hydrochloride | Reactions of Step(B)-(i) |

| Compound | Reaction(s) by which the compound is produced |
|---|---|
| hydrate. Melting point: 147–149° C | and (ii) |
| 3-Anilino-5-phenyl-2-(4-β-hydroxy-ethylpiperazino)methyl-2-cyclohexen-1-one hydrochloride ethanol adduct. Melting point: 110–112° C | Reactions of Step(B)-(i) and (ii) |
| 3-Anilino-5-phenyl-2-(N-methyl-N-benzylamino)methyl-2-cyclohexen-1-one hydrochloride. Melting point: 79–80° C | Reactions of Step(B)-(i) and (ii) |
| 3-(2-Chloroanilino)-5-phenyl-2-dimethylaminomethyl-2-cyclohexen-1-one hydrochloride. Melting point: 158–160° C | Reactions of Step(B)-(i) and (ii) |
| 3-(2-Chloroanilino)-5-phenyl-2-piperidinomethyl-2-cyclohexen-1-one hydrochloride. Melting point: 153–154° C | Reactions of Step(B)-(i) and (ii) |
| 3-(2-Chloroanilino)-5-phenyl-2-morpholinomethyl-2-cyclohexen-1-one hydrochloride ½ hydrate. Melting point: 178–179° C(decomp.) | Reactions of Step(B)-(i) and (ii) |
| 3-(2-Chloroanilino)-5-phenyl-2-(4-methylpiperazino)methyl-2-cyclo-hexen-1-one hydrochloride. Melting point: 187–189° C | Reactions of Step(B)-(i) and (ii) |
| 3-(2-Chloroanilino)-5-phenyl-2-(4-methylpiperidino)methyl-2-cyclo-hexen-1-one hydrochloride. Melting point: 165–167° C | Reactions of Step(B)-(i) and (ii) |
| 3-(2-Chloroanilino)-5-phenyl-2-(3-methylpiperidino)methyl-2-cyclo-hexen-1-one hydrochloride hydrate. Melting point: 141–143° C | Reactions of Step(B)-(i) and (ii) |
| 3-(4-Chloroanilino)-5-phenyl-2-dimethylaminomethyl-2-cyclohexen-1-one hydrochloride. Melting point: 183–184° C | Reactions of Step(B)-(i) and (ii) |
| 3-(4-Chloroanilino)-5-phenyl-2-diethylaminomethyl-2-cyclohexen-1-one hydrochloride hydrate. Melting point: 73–74° C | Reactions of Step(B)-(i) and (ii) |
| 3-(4-Chloroanilino)-5-phenyl-2-piperidinomethyl-2-cyclohexen-1-one hydrochloride hydrate. Melting point: 135–137° C | Reactions of Step(B)-(i) and (ii) |
| 3-(4-Chloroanilino)-5-phenyl-2-morpholinomethyl-2-cyclohexen-1-one hydrochloride hydrate. Melting point: 159–161° C | Reactions of Step(B)-(i) and (ii) |
| 3-(4-Chloroanilino)-5-phenyl-2-(4-β-hydroxyethylpiperazino)methyl-2-cyclohexen-1-one hydrochloride ½ hydrate. Melting point: 133–134° C | Reactions of Step(B)-(i) and (ii) |
| 3-(4-Chloroanilino)-5-phenyl-2-(N-methyl-N-benzylamino)methyl-2-cyclohexen-1-one hydrochloride hydrate. Melting point: 136–137° C | Reactions of Step(B)-(i) and (ii) |
| 3-(4-Methoxyanilino)-5-phenyl-2-piperidinomethyl-2-cyclohexen-1-one hydrochloride. Melting point: 140–141° C | Reactions of Step(B)-(i) and (ii) |
| 3-(4-Methoxyanilino)-5-phenyl-2-morpholinomethyl-2-cyclohexen-1-one hydrochloride. Melting point: 146–148° C | Reactions of Step(B)-(i) and (ii) |
| 3-(4-Methoxyanilino)-5-phenyl-2-dimethylaminomethyl-2-cyclohexen-1-one hydrochloride. Melting point: 170–171° C | Reactions of Step(B)-(i) and (ii) |
| 3-(4-Methoxyanilino)-5-phenyl-2-diethylaminomethyl-2-cyclohexen-1-one hydrochloride. Melting point: 141–131– C | Reactions of Step(B)-(i) and (ii) |
| 3-(4-Methoxyanilino)-5-phenyl-2-(4-β-hydroxyethylpiperazino)methyl-2-cyclohexen-1-one hydrochloride ½ hydrate. Melting point: 118–120° C | Reactions of Step(B)-(i) and (ii) |
| 3-(4-Methoxyanilino)-5-phenyl-2-(N-methyl-N-benzylamino)methyl-2-cyclohexen-1-one hydrochloride methanol adduct. Melting point: 115–120° C | Reactions of Step(B)-(i) and (ii) |
| 3-(2-Ethoxyanilino)-5-phenyl-2-piperidinomethyl-2-cyclohexen-1-one hydrochloride. Melting point: 170–171° C | Reactions of Step(B)-(i) and (ii) |
| 3-(4-Ethoxyanilino)-5-phenyl-2-dimethylaminomethyl-2-cyclohexen-1-one hydrochloride. Melting point: 161–162° C | Reactions of Step(B)-(i) and (ii) |
| 3-(4-Ethoxyanilino)-5-phenyl-2-diethylaminomethyl-2-cyclohexen-1-one hydrochloride. Melting point: 131– 133° C | Reactions of Step(B)-(i) and (ii) |
| 3-(4-Ethoxyanilino)-5-phenyl-2-piperidinomethyl-2-cyclohexen-1-one hydrochloride. Melting point: 175–176° C(decomp.) | Reactions of Step(B)-(i) and (ii) |
| 3-(4-Ethoxyanilino)-5-phenyl-2-morpholinomethyl-2-cyclohexen-1-one hydrochloride hydrate. Melting point: 160.5–162° C(decomp.) | Reactions of Step(B)-(i) and (ii) |
| 3-(4-Ethoxyanilino)-5-phenyl-2-(4-β-hydroxyethylpiperazino)methyl-2-cyclohexen-1-one dihydrochloride hydrate. Melting point: 170–172° C(decomp.) | Reactions of Step(B)-(i) and (ii) |
| 3-(4-Ethoxyanilino)-5-phenyl-2-(N-methyl-N-benzylamino)methyl-2-cyclohexen-1-one hydrochloride ½ hydrate. Melting point: 110–111° C(decomp.) | Reactions of Step(B)-(i) and (ii) |
| 3-(2-Methylanilino)-5-phenyl-2-piperidinomethyl-2-cyclohexen-1-one hydrochloride ½ ethanol adduct. Melting point: 136–138° C | Reactions of Step(B)-(i) and (ii) |
| 3-(2-Methylanilino)-5-phenyl-2-(4-methylpiperazino)methyl-2-cyclohexen-1-one hydrochloride. Melting point: 195–198° C(decomp.) | Reactions of Step(B)-(i) and (ii) |
| 3-(2-Methylanilino)-5-phenyl-2-(2-methylpiperidino)methyl-2-cyclohexen-1-one hydrochloride acetone adduct. Melting point: 115–118° C | Reactions of Step(B)-(i) and (ii) |
| 3-(2-Methylanilino)-5-phenyl-2-(4-methylpiperidino)methyl-2-cyclo-hexen-1-one hydrochloride. Melting point: 171–173° C(decomp.) | Reactions of Step(B)-(i) and (ii) |
| 3-Ethylamino-5-phenyl-2-dimethylamino-methyl-2-cyclohexen-1-one hydrochloride. Melting point: 149–150° C | Reactions of Step(B)-(i) and (ii) |
| 3-Ethylamino-5-phenyl-2-morpholino-methyl-2-cyclohexen-1-one hydrochloride. Melting point: 113° C | Reactions of Step(B)-(i) and (ii) |
| 3-Ethylamino-5-phenyl-2-(N-methyl-N-benzylamino)methyl-2-cyclohexen-1-one hydrochloride ½ hydrate. Melting point: 140–142° C | Reaction of Step(B)-(i) and (ii) |
| 3-Phenyethylamino-5-phenyl-2-dimethyl-aminomethyl-2-cyclohexen-1-one hydrochloride ½ hydrate. Melting point: 132° C | Reactions of Step(B)-(i) and (ii) |
| 3-Phenethylamino-5-phenyl-2-diethyl-aminomethyl-2-cyclohexen-1-one hydrochloride. Melting point: 124–125° C | Reactions of Step(B)-(i) and (ii) |
| 3-Phenethylamino-5-phenyl-2-piperidinomethyl-2-cyclohexen-1-one hydrochloride. Melting point: 113–114° C | Reactions of Step(B)-(i) and (ii) |
| 3-Phenethylamino-5-phenyl-2-morpholinomethyl-2-cyclohexen-1-one hydrochloride hydrate. Melting point: 120° C | Reactions of Step(B)-(i) and (ii) |
| 3-Phenethylamino-5-phenyl-2-(4-β-hydroxyethylpiperazino)methyl-2-cyclohexen-1-one hydrochloride ½ hydrate. Melting point: 132–135° C | Reactions of Step(B)-(i) and (ii) |
| 3-Phenethylamino-5-phenyl-2-(N-methyl-N-benzylamino)methyl-2-cyclohexen-1-one hydrochloride. Melting point: 142° C | Reactions of Step(B)-(i) and (ii) |
| 3-(3-methoxyanilino)-2-(N-methyl-N-benzylamino)methyl-2-cyclohexen-1-one hydrochloride. Melting point: 136–138° C(decomp.) | Reaction of Step(B)-(i) |
| 3-(2-Methylamino)-2-(N-methyl-N-benzylamno)methyl-2-cyclohexen-1- | Reaction of Step(B)-(i) |

| Compound | Reaction(s) by which the compound is produced |
|---|---|
| one hydrochloride. Melting point: 166–167° C(decomp.) | |
| 3-(2-Methoxyanilino)-2-pyrrolidino-methyl-5-phenyl-2-cyclohexen-1-one. Melting point: 150–151° C | Reaction of Step(B)-(i) |
| 3-(2-Chloroanilino)-2-pyrrolidino-methyl-5-phenyl-2-cyclohexen-1-one hydrochloride hydrate. Melting point: 165–166° C | Reaction of Step(B)-(i) |
| 3-(2-Methylanilino)-2-pyrrolidino-methyl-5-phenyl-2-cyclohexen-one. Melting point: 140–141° C | Reactions of Step(B)-(i) |
| 3-(3-Methoxyanilino)-5,5-dimethyl-2-(N-methyl-N-allylamino)methyl-2-cyclohexen-1-one hydrochloride. Melting point: 88–91° C | Reaction of Step(B)-(i) |
| 3-(3-Chloroanilino)-5,5-dimethyl-2-(N-methyl-N-allylamino)methyl-2-cyclohexen-1-one hydrochloride. Melting point: 106–109° C | Reaction of Step(B)-(i) |
| 3-(2-Methylanilino)-5,5-dimethyl-2-benzylaminomethyl-2-cyclohexen-1-one hydrochloride. Melting point: 195–197° C(decomp.) | Reaction of Step(B)-(i) |
| 3-Piperidino-5,5-dimethyl-2-morpholinomethyl-2-cyclohexen-1-one. Melting point: 99–101° C | Reaction of Step(B)-(i) |
| 3-(3-Chloroanilino)-5,5-dimethyl-2-(N-methyl-N-phenethylamino)methyl-2-cyclohexen-1-one. Melting point: 105–165° C(decomp.) | Reaction of Step(B)-(i) |
| 3-(N-dimethylamino-5,5-dimethyl-2-butylaminomethyl-2-cyclohexen-1-one. | Reaction of Step(B)-(i) |
| 3-(N-methyl-N-benzylamino)-5,5-dimethyl-2-propylaminomethyl-2-cyclohexen-1-one | Reaction of Step(B)-(i) |
| 3-(3-Nitroanilino)-5,5-dimethyl-2-piperidinomethyl-2-cyclohexen-1-one | Reaction of Step(B)-(i) |
| 3-(3-Acetylaminoanilino)-5,5-dimethyl-2-dimethylaminomethyl-2-cyclohexen-1-one | Reaction of Step(B)-(i) |
| 3-(3-Methylaminoanilino)-5,5-dimethyl-2-dimethylaminomethyl-2-cyclohexen-1-one | Reaction of Step(B)-(i) |
| 3-(3-Dimethylaminoanilino)-5,5-dimethyl-2-dimethylaminomethyl-2-cyclohexen-1-one | Reaction of Step(B)-(i) |
| 3-(2-Chloroanilino)-5,5-dimethyl-2-(4-hydroxypiperidino)methyl-2-cyclohexen-1-one | Reaction of Step(B)-(i) |
| 3-(3-Methoxyanilino)-5,5-dimethyl-2-(4-chloropiperidino)methyl-2-cyclohexene-1-one | Reaction of Step(B)-(i) |
| 3-(3-Methoxyanilino)-5,5-dimethyl-2-(4-methoxypiperidino)methyl-2-cyclohexen-1-one | Reaction of Step(B)-(i) |

EXAMPLE 9

Some examples of practical recipes in which the compound of the present invention are utilized as analgesics are as follows:

A. (Tablet)
| | | |
|---|---|---|
| (1) | 3-(3-methoxyanilino)-5,5-dimethyl-2-(N-methyl-N-phenethylamino)methyl-2-cyclohexen-1-one hydrochloride | 10 mg. |
| (2) | lactose | 35 mg. |
| (3) | corn starch | 150 mg. |
| (4) | microcrystalline cellulose | 30 mg. |
| (5) | magnesium stearate | 5 mg. |
| | | 230 mg. per tablet |

(1), (2), (3), ⅔ quantity of (4) and half quantity of (5) are throughly mixed, and then the mixture is granulated. Remaining ⅓ quantity of (4) and half of (5) are added to the qranules and compressed into tablets. Thus prepared tablets can further be coated with a suitable coating agent, e.g. sugar.

B. (Capsule)
| | | |
|---|---|---|
| (1) | 3-(3-methoxyanilino)-5,5-dimethyl-2-(N-methyl-N-phenethylamino)methyl-2-cyclohexen-1-one hydrochloride | 10 mg. |
| (2) | lactose | 102 mg. |
| (3) | microcrystalline cellulose | 70 mg. |
| (4) | magnesium stearate | 8 mg. |
| | | 190 mg. per capsule |

(1), (2), (3) and half quantity of (4) are throughly mixed, and then the mixture is granulated. Remaining half of (4) is added to the granules and the whole is filled into a gelatin capsule.

C. (Injection)
| | | |
|---|---|---|
| (1) | 3-(3-methoxyanilino)-5,5-dimethyl-2-(N-methyl-N-phenethylamino)methyl-2-cyclohexen-1-one hydrochloride | 5 mg. |
| (2) | inositol | 100 mg. |
| (3) | benzyl alcohol | 20 mg. |

All ingredients are dissolved in water to make 2.0 ml of the solution (pH 7.5) serving as injection.

REFERENCE EXAMPLE 1

16.2 Parts of a 37% aqueous solution of formaldehyde is cooled well with a refrigerating agent, and while the internal temperature is maintained at a temperature not exceeding 5° C, 14.6 parts of diethylamine is added dropwise, with stirring. At temperatures not exceeding 5° C, the whole mixture is stirred for 2 and a half hours. Then, anhydrous potassium carbonate is added to the resulting reaction mixture so as to cause produced diethyamonomethanol to separate. The separated oil are collected and dried over anhydrous potassium carbonate, whereby a colorless, clear solution of diethyaminomethanol is obtained. The resulting compound is identified by the data of magnetic nuclear resonance spectrum and infrared absorption spectrum.

What we claim is:

1. A member selected from the group consisting of a compound of formula $$\begin{array}{c}\text{structure with substituents } R^1, R^2, R^3, R^4, R^5, R^6\end{array}$$

wherein each of
R$^1$ and R$^2$ represents hydrogen, or methyl or when one of R$^1$ or R$^2$ is hydrogen the other may represent phenyl, one of R$^3$ and R$^4$ represents hydrogen, alkyl of 1 to 6 carbon atoms, and the other represents alkyl of 1 to 6 carbon atoms, benzyl, phenethyl, phenyl or phenyl mono-substituted by a member of the group consisting of alkyl of 1 to 3 carbon atoms, alkoxy of 1 to 3 carbon atoms, halogen, nitro and hydroxy, R$^5$ and R$^6$ represent piperidino, or piperidino mono-substituted by a member of the group consisting of alkyl of 1 to 3 carbon atoms, alkoxy of 1 to 3 carbon atoms, halogen, and hydroxy, with the proviso that the alkoxy, halogen and hydroxy substituent is in the 4-position of the piperidino nucleus and a pharmaceutically acceptable salt thereof.

2. A compound according to claim 1, wherein $R^1$ and $R^2$ are hydrogen.

3. A compound according to claim 1, wherein $R^1$ and $R^2$ are methyl.

4. A compound according to claim 1, wherein one of $R^1$ and $R^2$ is methyl and the other is hydrogen.

5. A compound according to claim 1, wherein one of $R^1$ and $R^2$ is hydrogen and the other is phenyl.

6. A compound according to claim 1, wherein one of $R^3$ and $R^4$ is hydrogen and the other is substituted phenyl.

7. A compound according to claim 1, wherein one of $R^3$ and $R^4$ is hydrogen and the other is lower alkyl.

8. A compound according to claim 1, wherein one of $R^3$ and $R^4$ is hydrogen and the other is benzyl or phenethyl.

9. A compound according to claim 1 wherein the compound is 3-(2-chloroanilino)-5,5-dimethyl-2-piperidinomethyl -2-cyclohexene-1-one.

10. A compound according to claim 1, wherein the compound is 3-(3-chloroanilino)-5,5-diemthyl-2-piperidinomethyl -2-cyclohexene-1-one.

11. A compound according to claim 1 wherein the compound is 3-(3-methoxyanilino)-5,5-dimethyl-2-piperidinomethyl -2-cyclohexene-1-one.

12. A compound according to claim 1 wherein the compound is 3-(4-methoxyanilino)-5,5-dimethyl-2-piperidinomethyl-2-cyclohexene-1-one.

* * * * *